United States Patent [19]

Kessler et al.

[11] Patent Number: 4,714,673

[45] Date of Patent: Dec. 22, 1987

[54] METHOD FOR MEASUREMENT OF CONCENTRATION OF SUBSTANCE

[76] Inventors: Manfred Kessler, An der Hornwiesen 50; Jens Höper, Moorbachweg 28, both of D-8520 Erlangen, Fed. Rep. of Germany

[21] Appl. No.: 648,883

[22] Filed: Sep. 10, 1984

[30] Foreign Application Priority Data

Sep. 10, 1983 [DE] Fed. Rep. of Germany ....... 3332745

[51] Int. Cl.$^4$ ............................................... C12Q 1/54
[52] U.S. Cl. ...................................... 435/14; 435/291; 435/817; 204/415; 204/418
[58] Field of Search ................... 435/288, 291, 14, 28, 435/817; 204/403, 415, 418, 1 E, 1 T; 128/635

[56] References Cited

U.S. PATENT DOCUMENTS

| 3,743,588 | 7/1973 | Brown et al. | 204/403 |
| 4,263,115 | 4/1981 | Kessler et al. | 204/415 |
| 4,276,141 | 6/1981 | Hawkins | 204/418 |
| 4,349,426 | 9/1982 | Sugahara et al. | 204/418 |
| 4,519,973 | 5/1985 | Cahalan et al. | 204/418 |

Primary Examiner—James C. Yeung
Assistant Examiner—Noah Kamen
Attorney, Agent, or Firm—Michael J. Striker

[57] ABSTRACT

A method for measurement of the concentration of a substance diffusable through inert membranes has a measuring electrode of metal, an electrolyte chamber containing electrolyte, a lipophilous membrane partially covering the measuring electrode and located between the measuring electrode and the electrolyte, and a reference electrode, wherein the substance is $H_2O_2$, the combined membrane contains lipophilous ions and/or carrier-bound ions, the base membrane is proton impermeable, and the measuring electrode is formed as anode.

23 Claims, 2 Drawing Figures

H₂   O₂

GLUCOSE

METHOD FOR MEASUREMENT OF CONCENTRATION OF SUBSTANCE

BACKGROUND OF THE INVENTION

The present invention relates to a device or method for measurement of the concentration of a substance. More particularly, it relates to a device or method for measurement of the concentration of a substance which is diffusable through inert membranes.

Devices of the above mentioned general type are known in the art. One of such devices is disclosed, for example, in the U.S. Pat. No. 4,263,115. The device disclosed in this patent has a reduction electrode for the oxygen composed of a noble metal and connected to a voltage source, and a reference electrode annularly disposed about the reduction electrode. A ligand membrane is provided in front of the reduction electrode and contains a cationselective carrier and is permeable to hydrogen ions. A closure membrane to seal the electrodes against the outside space is provided permeable to oxygen and impermeable to water. An aqueous electrolyte containing the ligand cation of the ligand membrane is disposed between the ligand membrane and the closure membrane. The known arrangement is advantageous for the concentration measurement especially because with the provision of a protective membrane on the electrode, larger electrodes can be used, which is thereby cheaper, simpler to manufacture and handle, and have smaller impedance, without the problem of diffusion gradient which conventionally takes place in large electrodes and so that damaging substances which do not belong to measurement reaction can be retained far from the electrode. It is desirable to form these arrangements so as to enable it to measure also the concentration of other important, especially physiologically important, substances.

SUMMARY OF THE INVENTION

In keeping with these objects and with others which will become apparent hereinafter, one feature of the present invention resides, briefly stated, in a method for measurement of the concentration of a substance diffusable through inert membranes and susceptible to redox reactions with a measuring electrode of metal, preferably noble metal, a lipophilous membrane which partially covers the measuring electrode and located between the measuring electrode and an electrolyte accommodated in an electrolyte chamber, and a reference electrode wherein the substance to be measured is in the electrolyte chamber, in which in accordance with the present invention the substance to be measured is $H_2O_2$, the combined membrane contains lipophilous ions and/or carrier bound ions, the base membrane is proton-impermeable, and the measuring electrode is formed as anode.

The fact that the substance to be measured is in the electrolyte chamber means that it is diffusable from a medium in which its concentration finally must be determined, or is produced in the electrolyte chamber, as will be explained hereinbelow. The fact that the measuring electrode is formed as anode especially means that it acts as anode by the polarization voltage or by the suitable selection of the reference electrode.

The base membrane is a membrane before joining of the lipophilous ions and/or the carrier, preferably of polyvinylchloride or silicon rubber, whereas the combined membrane is the membrane after joining.

With this development it is possible to measure exactly the concentration of the $H_2O_2$, specially important as physiological "waste product" in a simple manner, without drift phenomena and without errors because of a diffusion gradient. It is surprising that a proton impermeability enables the measurement of $H_2O_2$. The reactions which take place during the oxidation of $H_2O_2$ and in this device are still not clear in detail.

In accordance with a further feature which is especially advantageous and provides for a favorable reaction condition, the ions are anions. The high transconductance is obtained with a specially advantageous hexa-decyl-pridinium-chloride. It is suspected that the anions can advantageously contribute to formation of a polarization layer at the border of electrodes-protective membrane. Also the carrier-bound ions can be anions and contained also then in the electrolyte.

In accordance with an especially advantageous feature, the carrier-bound ions can be cations, particularly potassium ions. Potassium ions are first of all especially favorable since the potassium content of physiological liquids is substantially constant and thereby when the arrangement is brought in connection with such liquids for measurement of the partial pressure, foreseeable diffusion conditions can take place or the electrolyte which also contains the carrier-bound ions can be suitably adjusted since the potassium content is often known in advance. There is also no osmosis problem.

It is especially advantageous when the carrier is valiomycin. This carrier has proven itself in the practice. Furthermore, it is especially matching with the potassium.

Advantageously, the carrier is a cation carrier of high mobility and specific, especially for protons, such as preferably tri-n-dodecyl-amine. With a cation carrier of the tri-n-dodecylamine, which advantageously complexes the protons very fast response and decay times of measuring values are obtained.

The proton impermeability is the practical proton impermeability of the base membrane, for example of polyvinylchloride, without additives.

Depending upon the type of the additives a different condition of the combined membrane is obtained.

1. The membrane contains only lipophilous ions, for example the hexa-decyl-pyridinium-chloride acting as a buffer (proton acceptor). Here the combined membrane is practically proton impermeable, in other words within the limits of an $H^+$-ion permeability, which is required for an off-reaction of an electrode with fast decay time, the polyvinylchloride combined membrane with hexa-decyl-pyridinium-chloride is also practically proton impermeable.

A relatively fast raise of the measuring value is obtained, and it is maintained for several hours, in the order to 12 hours. Such a design is advantageous for the one-time measurement by throw-away injection electrodes whose measurements must be processed with a subsequent system since the measuring value raises longer. This membrane is especially advantageous because of its low cost.

2. The membrane contains a carrier, for example valinomycin, which because of its even small, transverse permeability to protons transports them. The $H^+$-complexion takes place here at the electrode limiting surface relatively fast, however, since practically no bucket chain phenomenon takes place, the proton emission is delayed. Then there is obtained a relatively fast raising time of the measuring value, but a somewhat faster decay time, for example two hours, as in the case of, for example, the hexa-decyl- pyridinium-chloride. These features of the combined membranes which maintain the measuring value for the processing also longer, are useable repeatedly in the course of the day.

3. The membrane contains a proton carrier of high mobility. Then there are obtained fast raise and decay times, that is favorable for continuous measurements.

In accordance with an especially advantageous feature, a polarization voltage source is provided, whose plus pole is connected with the measuring electrode. It has been determined that the arrangement operates especially favorably with a polarization voltage. However, it is also possible to omit this. Then, by the selection of the reference electrode, it must be guaranteed that the measuring electrode is the anode.

It is especially advantageous when the closure membrane is permeable for $H_2O_2$. Thereby, a diffusion of the material to be measured in the electrolyte chamber is possible, with which an equilibrium is adjusted which then in turn is measured by the device via the $H_2O_2$ oxidated on the measuring electrode. For this, the polytetrafluoroethylene is especially recommended.

In accordance with an especially advantageous feature of the invention, the electrolyte chamber is formed as a reaction chamber which has in it an enzyme which converts a substance diffusable through the closure membrane into the electrolyte with formation of $H_2O_2$. With this feature it is possible in a very simple and advantageous manner to measure the concentration especially of important physiological substances. Since the substance is diffusable through the closure membrane into the electrolyte, with the closure membrane permeable for this substance, an equilibrium between the substance in the liquid to be measured and in the electrolyte is formed when the device is brought via the closure membrane in contact with a liquid which contains the substance to be measured, for example, body liquid, in vivo or in vitro. By the selection of a suitable enzyme, $H_2O_2$ is formed from the substance with a concentration which is then measured with the aid of the membrane-coated measuring electrode, whereby a magnitude of the concentration of the substance in the liquid to be measured is produced. The closure membranes in such cases are porous membranes.

The enzyme is advantageously in aqueous solution. Alternatively, it can be however structurally bound.

Advantageously, the closure membrane is permable for small molecules, whereas for large molecules in contrast it is impermeable. That means it is a porous membrane. Thereby it is prevented that the enzyme diffuses from the electrolyte chamber-reaction chamber into a chamber to be measured or another damaging enzyme which is responsible for conversion of another substance gets into the electrolyte chamber. "The small molecules" are here molecules up to a molecular weight of approximately $10^4$ Dalton, whereas the "large molecules" are molecules with a molecular weight greater than $10^4$ Dalton. In individual cases, the pore dimension is selected correspondingly so as to provide permeability only for desired substances and impermeability for undesired substances.

Advantageously the enzyme is glucose-oxidase, and the closure membrane is permeable for glucose and glucon-acid-lactone. The measurement of the glucose content in blood or other body liquids is of exceptional importance in view of great and growing number of diabetic patients. With the given features, an arrangement is provided which determines the glucose concentration in liquids with up to now impossible simplicity and speed and high accuracy without the necessity of checking in short intervals (up to now frequently minute interval). The above described advantages can be used especially favorably when the device, in some cases and advantageously including the polarization voltage source, is formed as an integrated implantable unit and has transmitter or sender for the measurement results. Such a device can particularly cooperate in an especially advantageous manner with recently developed implantable dosing pumps for insulin. Furthermore the user can be given a direct warning signal which indicates that the useable region of the glucose concentration in blood is not reached or exceeded.

It is especially advantageous when the reference electrode is a noble metal electrode connected as a cathode and covered with a membrane which advantageously contains a proton ligand, preferably tri-n-dodecylamine. Thereby the accuracy of the measurement is further improved.

As a special advantage of the invention it is noted that the obtained measuring value, or the obtained signal amounts to approximately double the signal which is expected in accordance with the Nernst potential equation for a 2-electron reaction.

It is especially advantageous when the lipophilous base membrane is composed of polyvinylchloride or silicon rubber. It has been shown that with the use of such a base membrane, a doubling of the Nernst potential takes place.

With the oxidation of $H_2O_2$ in accordance with the reaction equation:

$$H_2O_2 - 2e^- \rightarrow O_2 + 2H^+$$

a EMK is obtained of 59 mV/Dekade (at 25° C).

Obviously with these operations two stable series potential parts can be formed. This causes a signal gain of 100%.

It is especially advantageous when base membranes are used with small membrane thickness, particularly with a membrane thickness of 10–50 micrometer.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
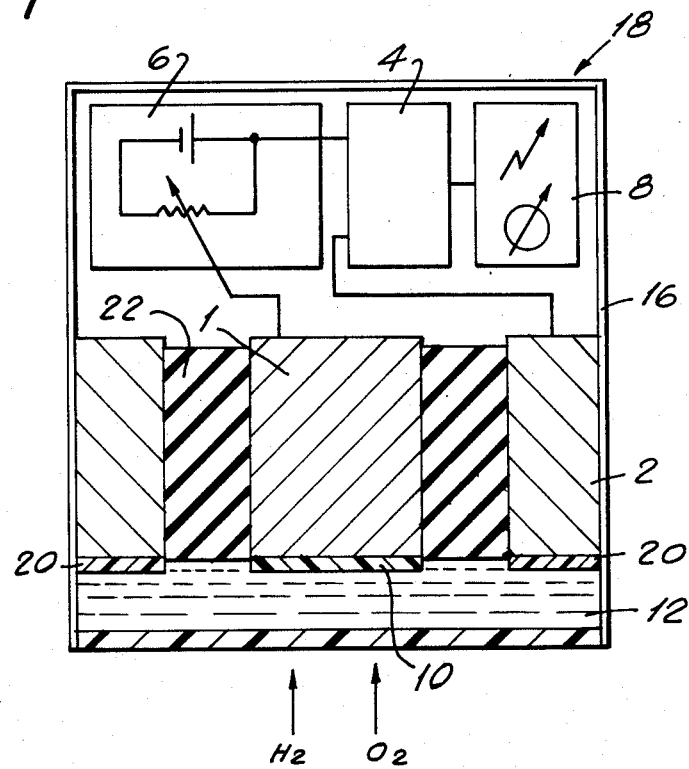
FIG. 1 is a view schematically showing a device in accordance with the present invention, in section.

A device for measurement of the concentration of a substance by a method in accordance with the invention shown in FIG. 1 has a measuring electrode 1 which is composed preferably of gold, but also can be composed of platinum, and a reference electrode 2 which is advantageously ring-shaped. The measuring electrode 1 is connected with the plus pole and the reference electrode 2 is connected with the minus pole of a polarization voltage source 6. The reference electrode 2 is connected to this minus pole via a measuring amplifier 4 with an input resistance of about $10^{12}$ Ω (for the case of the potential measurement) of a measuring resistance of $10^6$ Ω (for the case of the amperometric measurement).

The voltage value or current value measured by the measuring mechanism 4 is displayed on an indicating element 8 which is provided, as shown symbolically, with a distant transmitter, for example a sender. This sender sends the measured value for example to a not shown microprocessor which computes with the consideration of the details of the measuring conditions the concentration of the $H_2O_2$ to be measured and used the computed value in some cases for obtaining a further value which is again delivered. A protective membrane 10 of a lipophilous material, for example polyvinylchloride covers the measuring electrode (anode) 1 from an electrolyte 12 contained in an electrolyte chamber. The membrane 10 is treated by admixing a suitable salt with lipophilous anions. As mentioned above, the salt can be hexa-decyl-phridinium-chloride. It is further $H^+$ impermeable. The carrier bound ions contained in the membrane are also in the electrolyte 12.

The reference electrode 2 is advantageously a Ag-AgCl-electrode or a calomel electrode. It can also be provided with a protective reference electrode membrane, which however does not have to be used. The electrolyte 12 covers the protective electrode arrangement. The electrolytic chamber is closed substantially at the side facing away from the electrodes by an $H_2O_2$ permeable water-impermeable membrane 14, for example, 25-100 micron polytetrafluoroethylene. When this membrane adjoins a medium containing $H_2O_2$, then because of diffusion an equilibrium is formed between the $H_2O_2$ in the outer space and the electrolyte. The $H_2O_2$ reaches into the electrolyte partially through the membrane 10 on the measuring electrode and is there oxidized. The thus produced potential or the thus produced current is measured and supplies a magnitude for the $H_2O_2$ concentration. An insulating inert material 22 is located between the electrodes 1 and 2.

Figure 2:
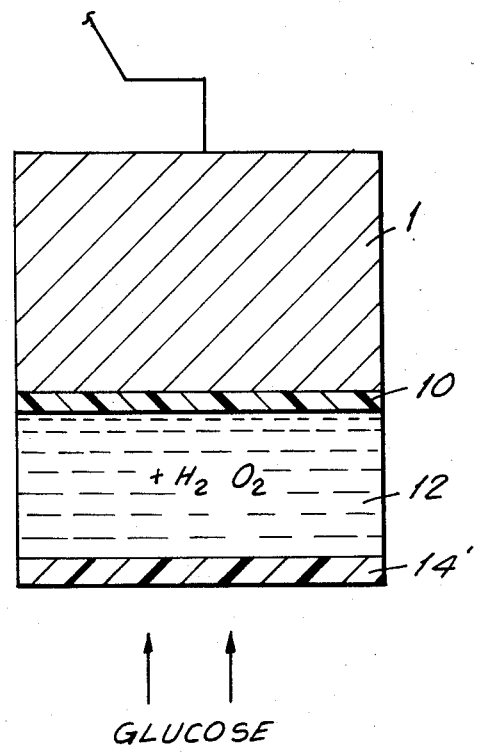
FIG. 2 is a view schematically showing a part of the device in accordance with FIG. 1 to illustrate a further embodiment of the invention.

The entire device, except the outer surface of the membrane 14 can be enclosed which is especially advantageous with the embodiment shown in FIG. 2.

In FIG. 2 the measuring electrode 1 is again covered with the above described lipophilous polyvinylchloride membrane 10 from the electrolyte 12. The electrolyte contains in enzyme by which with the aid of an enzyme reaction from an associated substance a reaction product plus $H_2O_2$ is obtained. The closure membrane 14' is formed as a porous membrane so that the substance, for example, glucose, can diffuse through the membrane 55 and an equilibrium concentration of the substance is obtained also in the electrolyte. This substance is converted in the enzyme reaction, and in this embodiment the $H_2O_2$ provided first in the electrolyte chamber is also measured as in the embodiment of FIG. 1. This measurement allows inference to the quantity of the available substance. It is important that the end product produced in addition to $H_2O_2$, glucon-acid-lactone in the case of glucose and the enzyme glucose-oxidase can diffuse through the membrane 14' outwardly to avoid continuous enrichment in the electrolyte chamber and thereby displacement of the reaction equilibrium. In contrast, the membrane 14' must be impermeable for the enzyme-molecules to prevent errors in the measurement results.

With the embodiment of FIG. 2 the enclosed device of FIG. 1 can be implanted and can provide measurements for a long time, for example, measurements of the glucose concentration. The measurement results are supplied for example to a microprocessor either continuously or in some cases on order, via an enclosed signal receiver. This shows whether the useable region of the glucose concentration is not reached or exceeded. Then, for example, a warning signal can be produced or concrete measures can be taken (quantity of received nutrient medium), so as to correct the non-equilibrium. Furthermore, an insulin pump can be controlled. With the device it is also possible to carry out amperometric measurements.

It will be understood that each of the elements described above, or two or more together, may also find a useful application in other types of constructions differing from the types described above.

While the invention has been illustrated and described as embodied in a device for measurement of the concentration of a substance, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method for determining the concentration of $H_2O_2$ by the steps of: providing a metal measuring electrode, a reference electrode, a proton impermeable lipophilous base membrane containing both a carrier and ions selected form the group consisting of lipophilious ions, carrier bound ions, and both lipophilious and carrier bound ions, and an electrolyte chamber containing an electrolyte; and locating said electrodes adjacent said chamber wherein said base membrane seals said measuring electrode from direct contact with said electrolyte; providing a polorization voltage across said electrodes; providing circuit indicating means operationaly connected to said electrodes; providing $H_2O_2$ in said electrolyte; and determining $H_2O_2$ concentration from said indicating means.

2. A method as defined in claim 1, wherein said ions provided are anions.

3. A method as defined in claim 1, wherein said carrier bound ions provided are cations.

4. A method as defined in claim 3, wherein said carrier bound ions provided are potassium ions.

5. A method as defined in claim 1, wherein said carrier provided is valinomycin.

6. A method as defined in claim 1, wherein said carrier provided is a cation carrier of high mobility and specific for protons.

7. A method as defined in claim 6, wherein said carrier provided is tri-ni-dodecylamine.

8. A method as defined in claim 1, wherein said voltage provided is by a polarization voltage source having a plus pole connected with said measuring electrode.

9. A method as defined in claim 1, and further providing a closure membrane arranged to close said electrolyte chamber from outside.

10. A method as defined in claim 9, wherein said closure membrane provided is permeable to $H_2O_2$.

11. A method as defined in claim 9, wherein said electrolyte chamber provided is also formed as a reaction chamber which contains an enzyme converting a substance diffusable through said closure membrane into said electrolyte with formation of $H_2O_2$.

12. A method as defined in claim 11, wherein said enzyme provided is in a water solution.

13. A method as defined in claim 11, wherein said enzyme provided is structure bound.

14. A method as defined in claim 11, wherein said closure membrane provided is permeable for small molecules and impermeable for large molecules.

15. A method as defined in claim 11, wherein said enzyme provided is glucose-oxidase, said closure membrane provided being permeable to glucose and gluconacid-lactone.

16. A method as defined in claim 1, wherein said electrodes, said base membrane and said chamber provided, together form an integrated implantable unit.

17. A method as defined in claim 1, wherein said electrodes with said base membrane and said chamber are provided with a polarization voltage source and together form an integrated implantable unit.

18. A method as define in claim 1, wherein said reference electrode provided is composed of a noble metal and formed as a cathode covered with a membrane.

19. A method as defined in claim 18, wherein said membrane which covers said reference electrode comprises a proton carrier.

20. A method as define in claim 18, wherein said membrane covering said reference electrode comprises tri-n-dodecylamine.

21. A method as defined in claim 1, wherein said base membrane provided is composed of polyvinylchloride.

22. A method as defined in claim 1, wherein said base membrane provided is composed of silicon rubber.

23. A method as defined in claim 1, wherein said measuring electrode provided is composed of a noble metal.

* * * * *